(12) United States Patent
Edelman (10) Patent No.: US 9,737,222 B2
(45) Date of Patent: Aug. 22, 2017

(54) METHOD FOR NON-CONTRAST ENHANCED MAGNETIC RESONANCE ANGIOGRAPHY

(71) Applicant: Robert Edelman, Highland Park, IL (US)

(72) Inventor: Robert Edelman, Highland Park, IL (US)

(73) Assignee: ENH RESEARCH INSTITUTE, Evanston, IL (US)

( * ) Notice: Subject to any disclaimer, the term of this patent is extended or adjusted under 35 U.S.C. 154(b) by 107 days.

(21) Appl. No.: 14/717,728

(22) Filed: May 20, 2015

(65) Prior Publication Data

US 2016/0338600 A1    Nov. 24, 2016

(51) Int. Cl.
| | | |
|---|---|---|
| *A61B 5/02* | (2006.01) | |
| *A61B 5/026* | (2006.01) | |
| *A61B 5/00* | (2006.01) | |
| *G01R 33/483* | (2006.01) | |
| *G01R 33/563* | (2006.01) | |
| *G01R 33/56* | (2006.01) | |

(52) U.S. Cl.
CPC .......... *A61B 5/0263* (2013.01); *A61B 5/7207* (2013.01); *G01R 33/4838* (2013.01); *G01R 33/5635* (2013.01); *G01R 33/5607* (2013.01)

(58) Field of Classification Search
CPC    A61B 5/0263; A61B 5/7207; G01R 33/3607; G01R 33/4818

See application file for complete search history.

*Primary Examiner* — Bo J Peng
(74) *Attorney, Agent, or Firm* — Quarles & Brady LLP (57) ABSTRACT

A method for performing a non-contrast-enhanced magnetic resonance angiography ("MRA") for a subject is provided. The method includes directing a magnetic resonance imaging ("MRI") system to perform a pulse sequence to acquire k-space data from imaging slices that are oriented away from an axial direction of the subject. The method includes repeating the pulse sequence for a plurality of imaging slices, wherein a field-of-view ("FOV") of at least one of the plurality of imaging slices is shifted by a predetermined value. The method also includes reconstructing, using the acquired k-space data, one or more angiographic images indicative of the subject's vasculature.

20 Claims, 6 Drawing Sheets

METHOD FOR NON-CONTRAST ENHANCED MAGNETIC RESONANCE ANGIOGRAPHY

BACKGROUND

The present disclosure relates to magnetic resonance imaging ("MRI") and systems. More particularly, the present disclosure relates to methods for non-contrast enhanced magnetic resonance angiography ("MRA").

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

Magnetic resonance angiography ("MRA") uses the magnetic resonance phenomenon to produce images of the human vasculature. To enhance the diagnostic capability of MRA, a contrast agent such as gadolinium can be injected into the patient prior to the MRA scan. The goal of this contrast enhanced ("CE") MRA method is to acquire the central k-space views at the moment the bolus of contrast agent is flowing through the vasculature of interest in order to benefit from improved contrast. That is, collection of the central lines of k-space during peak arterial enhancement, therefore, is key to the success of a CE-MRA exam. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins.

In many anatomic regions, such as the carotid or renal arteries, the separation between arterial and venous enhancement can be as short as 6 seconds. Hence, short separation time dictates the use of acquisition sequences of either low spatial resolution or very short repetition times ("TR"). Short TR acquisition sequences severely limit the signal-to-noise ratio ("SNR") of the acquired images relative to those exams in which a longer TR is employed. The rapid acquisitions required by first pass CE-MRA methods thus impose an upper limit on either spatial or temporal resolution.

Recently, a rare and serious pathology involving fibrosis of skin, joints, eyes, and internal organs referred to as nephrogenic systemic fibrosis ("NSF") has been correlated to the administration of gadolinium-based contrast agents to patients undergoing contrast-enhanced MRA studies. The link between gadolinium-based contrast agents and NSF is described, for example, by P. Marckmann, et al., in "Nephrogenic Systemic Fibrosis: Suspected Causative Role of Gadodiamide Used for Contrast-Enhanced Magnetic Resonance Imaging," *J. Am. Soc. Nephrol.*, 2006; 17 (9):2359-2362. As a result of the increased incidence of NSF, methods for MRA that do not rely on the administration of a contrast agent to the patient have become an important field of research. However, current methods for non-contrast angiography are limited in their utility because they are sensitive to patient motion, do not consistently or accurately portray vessel anatomy in patients with severe vascular disease, and require excessively long scan times.

While single shot acquisition methods such as two-dimensional ("2D") balanced steady-state free precession ("bSSFP") have the potential to reduce motion artifacts and shorten exam times, arterial conspicuity is inadequate due to high background signal. Moreover, bSSFP methods do not lend themselves to the creation of maximum intensity projection ("MIP") angiograms. In one example, a saturation-recovery bSSFP pulse sequence employed for cardiac perfusion imaging following the administration of a paramagnetic contrast agent is described by W. G. Schreiber, et al., in "Dynamic Contrast-Enhanced Myocardial Perfusion Imaging Using Saturation-Prepared TrueFISP," *JMRI*, 2002; 16:641-652. However, this pulse sequence applies a spatially non-selective saturation pulse that suppresses the signal from blood and, thus, cannot be employed for MRA. Additionally, Schreiber's method does not provide a means for distinguishing arteries from veins.

It is, in fact, particularly challenging to suppress venous signal with a single shot acquisition because, unlike arterial blood, venous blood typically flows slowly or even, for periods of time, not at all. In addition, the venous flow pattern is largely unpredictable, sometimes varying with a patient's respiration cycle, cardiac cycle, or both. Consequently, it is problematic to eliminate the signals from veins with single shot acquisitions, because venous blood flows only a short distance or not at all during the short scan time. Unfortunately, venous signals tend to overlap with arterial signals on projection images, thereby making it difficult or impossible to diagnose arterial disease using such methods for MRA. In addition, a robust single shot non-contrast MRA technique must provide an accurate depiction of arterial anatomy over a wide range of flow velocities, ranging from a few centimeters per second ("cm/sec") to more than 100 cm/sec. Moreover, the arterial anatomy must be depicted with sufficient arterial conspicuity to allow creation of a projection angiogram.

Several approaches have been previously described to suppress venous signal on non-contrast MR angiograms as follows. One method for venous suppression has been accomplished using image subtraction. Techniques like fresh blood imaging ("FBI") involve the subtraction of two images with different arterial signals, but identical venous signals. In this manner, the venous, but not arterial, signals cancel with subtraction. Unlike the saturation-based methods, subtraction techniques eliminate the signals from both stationary and moving venous spins. However, image subtraction doubles scan time and greatly increases the sensitivity of the technique to patient motion. In addition, these methods require prior knowledge of flow velocities in order to maximize arterial conspicuity.

Another method for suppressing venous signals is to employ a $T_2$-weighted magnetization preparation pulse, which diminishes signal in veins because venous blood has a reduced oxygen tension. However, this method is inconsistently effective because the level of venous oxygenation varies widely and unpredictably.

Yet another method is to repeatedly apply a saturation radio frequency ("RF") pulse just prior to the pulse sequence used for data acquisition, and to repeat this process multiple times at typical intervals of 20-200 milliseconds ("ms"). However, the use of a single shot acquisition with subsecond data acquisition time does not afford the time to repeatedly apply a saturation RF pulse. As a result, this approach is only applicable to multi-shot acquisition techniques where the data is acquired over tens of seconds to several minutes. Moreover, the repeated application of RF pulses causes marked suppression of arterial signal in tortuous vessels, thereby limiting the diagnostic accuracy of these methods.

A single shot acquisition method for MRA is described by R. Edelman, et al., in "Fast Time-of-Flight MR Angiography with Improved Background Suppression," *Radiology*, 1991; 179:867-870. This method requires the use of an inversion recovery preparation pulse and relies on arterial inflow during the data acquisition period to produce arterial contrast. In this respect, the inversion time ("TI") is selected solely to match the center lines of k-space to the "null" point for the longitudinal magnetization of background tissue, and is not selected in order to allow for the inflow of arterial blood into the imaging slice. In other words, the purpose of the TI is to reduce the signal intensity of background tissues.

This method suffers from several drawbacks. For example, the method acquires data over a lengthy time period on the order of one second, thereby encompassing both systole and diastole. With this lengthy time period required for data acquisition, it is not possible to synchronize TI to the period of rapid, systolic arterial flow, nor to the period of slow diastolic flow. Moreover, the TI employed by Edelman is too short (on the order of 75 ms) to allow for substantial arterial inflow. As a result, most of the arterial inflow occurs during the application of repeated RF pulses. As described above, the repeated application of RF pulses in this manner causes marked suppression of arterial signal in tortuous vessels, thereby limiting the diagnostic accuracy of such methods for MRA. The method also does not allow for the effective suppression of venous or fat signals, which are both essential to accurately depict the arteries.

Other methods of non-contrast enhanced MRA are described, for example, by M. Katoh, et al., in "Free-Breathing Renal MR Angiography With Steady-State Free-Precession (SSFP) and Slab-Selective Spin Inversion: Initial Results," *Kidney International*, 2004; 66:1272-1278, and by Y. Yamashita, et al., in "Selective Visualization of Renal Artery Using SSFP with Time-Spatial Labeling Inversion Pulse: Non-Contrast Enhanced MRA for Patients with Renal Failure," *Proc. Intl. Soc. Mag. Reson. Med.* 13 (2005) p. 1715. The method described by Katoh utilizes a three-dimensional ("3D") acquisition with a pre-inversion of the 3D region, while Yamashita employs two inversion pulses (one spatially selective and the other spatially non-selective). Each of these methods uses inversion preparation pulses rather than saturation pulses and further requires the use of a 3D, rather than 2D, acquisition for MRA. Given the substantial thickness of the 3D imaging slab, inflowing unsaturated spins must travel a large distance (for example, up to several centimeters) to replace in-plane saturated ones. Consequently, there is poor depiction of slowly flowing arterial spins. In fact, the inversion time, TI, must be very long (on the order of 1 second) to provide adequate inflow of even moderately fast flowing arterial spins. The long TI spans both the systolic and diastolic phases of the cardiac cycle. Given the long TI, it is problematic to synchronize data acquisition to diastole. In addition, 3D acquisitions are too time-consuming to permit data acquisition within a single breath-holding period.

A 2D adaptation of Yamashita's "time-SLIP" acquisition is described by S. Yamada, et al., in "Visualization of Cerebrospinal Fluid Movement with Spin Labeling at MR Imaging: Preliminary Results in Normal and Pathophysiologic Conditions," *Radiology*, 2008; 249; 644-652. This method, however, is employed to image the flow of cerebrospinal fluid flow rather than for MRA applications. Additionally, it uses two inversion pulses, rather than saturation pulses, and has a very long TI (on the order of 2500 ms) that is incompatible with MRA studies.

It would therefore be desirable to provide a method for non-contrast enhanced MRA that produced images of a patient's vasculature in a relatively short duration of time while maintaining significant discrimination of the arteries and substantially suppressing venous signals.

SUMMARY

The present disclosure provides systems and methods that overcome the aforementioned drawbacks in non-contrast enhanced magnetic resonance angiography ("MRA"). In particular, the present disclosure describes an imaging approach that reduces the time for scanning a region of interest in a subject by utilizing one or more imaging slices oriented away from an axial direction of the subject. In some aspects, a field-of-view ("FOV") of at least one of the plurality of the imaging slices may be shifted in order to maintain alignment of the imaging slices with the vasculature being imaged.

In accordance with aspects of the present disclosure, a method for performing a non-contrast-enhanced magnetic resonance angiography ("MRA") for a subject is provided. The method includes directing a magnetic resonance imaging ("MRI") system to perform a pulse sequence to acquire k-space data from imaging slices that are oriented away from an axial direction of the subject. The pulse sequence includes applying at least one radio frequency ("RF") saturation pulse to a selected region in the subject at least partially suppressing magnetic resonance signals therein, and applying at least one RF saturation pulse to an imaging slice outside the selected region at least partially suppressing magnetic resonance signals therein. The pulse sequence also includes waiting a period of time sufficiently long to allow saturated vascular spins from the selected region to flow into the imaging slice and to allow unsaturated vascular spins from outside the selected region to flow into the imaging slice. The pulse sequence further includes acquiring k-space data from the imaging slice following, and repeating above pulse sequence steps for a plurality of imaging slices, wherein a field-of-view ("FOV") of at least one of the plurality of imaging slices is shifted by a predetermined value. The method also includes reconstructing, using the acquired k-space data, one or more angiographic images indicative of the subject's vasculature.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Contrast-enhanced magnetic resonance angiography ("CE-MRA") is frequently used to evaluate vascular disease, whereby a contrast agent, such as gadolinium, is injected into the patient prior to a MRA scan. However, use of contrast agents requires the timing of data acquisition with bolus passing through the vasculature of interest in order to benefit from improved contrast. In addition, contrast agents are not recommended for patients with reduced kidney function or renal failure. As such, non-enhanced MR angiography ("NE-MRA") is particularly advantageous, particularly for patients with impaired renal function. For thin-section NE-MRA techniques, such as 2D time-of-flight and quiescent interval ("QI") MRA, it would be desirable to minimize scan time so as to maximize patient comfort and imaging efficiency. Particularly for QI MRA, a shorter scan time has the additional benefit of reducing the length or number of breath-holds required for abdominal and pelvic imaging.

In the human body, certain blood vessels, such as the carotid and peripheral arteries are predominantly oriented in a cranio-caudal direction. As such, standard thin-section MRA techniques involve acquisition of images in an axial or near axial orientation so as to ensure maximum refreshment of vascular spins within each slice, as well as adequate venous suppression through the use of radiofrequency saturation pulses. However, the present disclosure recognizes that the number of slices utilized for imaging a region of interest in a subject may be reduced by modifying the orientation direction of the acquired imaging slices. That is, by tilting the imaging slices away from an axial direction of the subject, such as the craio-caudal direction, appreciable savings in scanning time may be achieved on account of fewer imaging slices being required to image the region of interest.

Figures 5A, 5B, 5C, 5D:
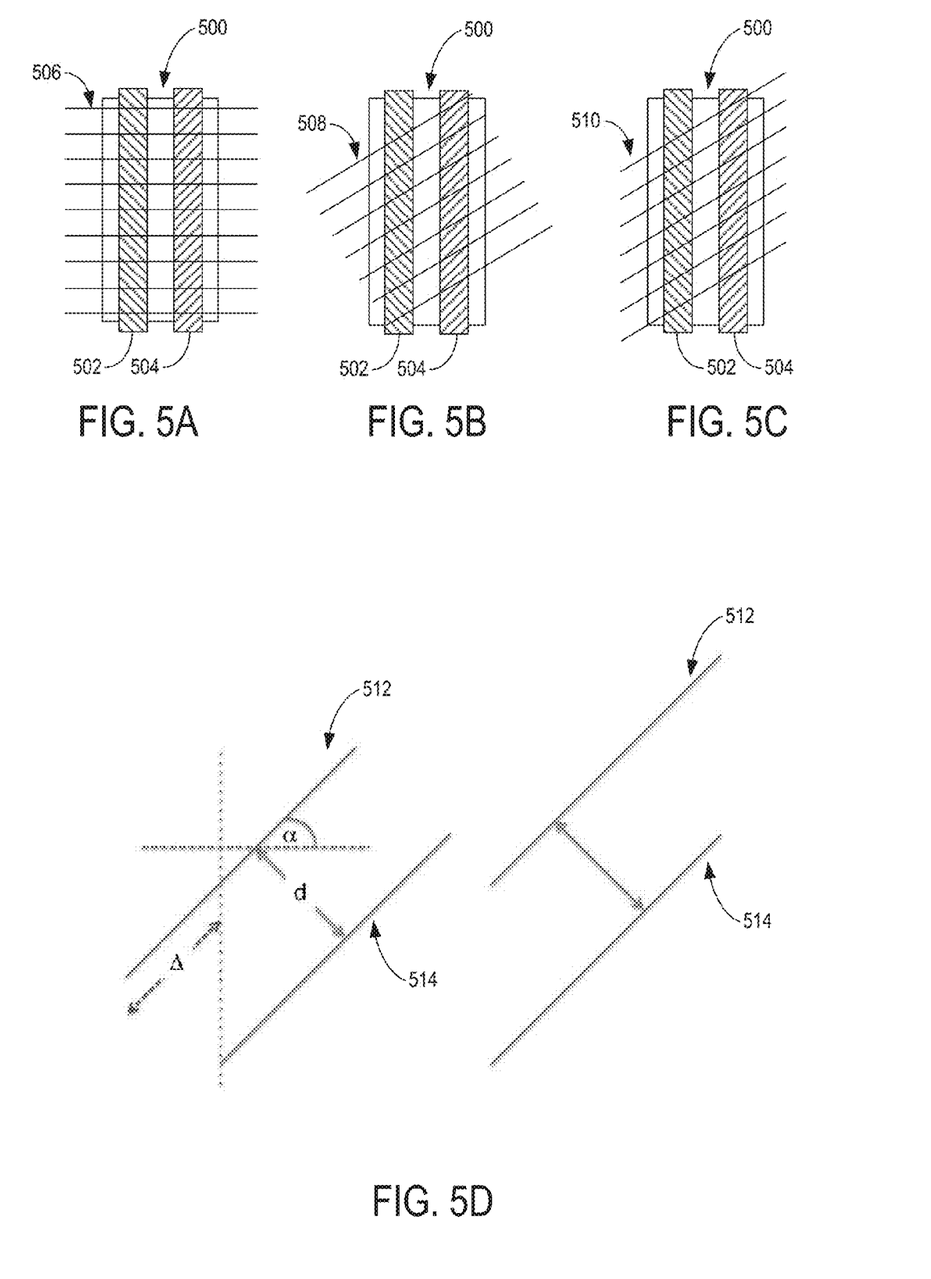
FIG. 5A is a schematic showing traditional axial imaging of vasculature.
FIG. 5B is a schematic showing an imaging strategy, in accordance with the present disclosure, where imaging slices are oriented away from an axial direction of the vasculature.
FIG. 5C is a schematic showing an imaging strategy, in accordance with the present disclosure, where imaging slices are oriented away from an axial direction of the vasculature and include field-of-view ("FOV") shifts for improved vasculature coverage.
FIG. 5D is a schematic showing two tilted imaging slices with and without a FOV shift.

To illustrate this point, refer to the schematic FIG. 5A, where an example imaging region 500, which includes an artery 502 and vein 504, is spanned by a group of imaging slices 506. As shown, the central axis of each of the imaging slices 506 is oriented substantially parallel to the vasculature in the imaging region 500. In this example, a total of 9 imaging slices 506 are shown to provide coverage of the imaging region 500. By orienting the imaging slices 506 away from the longitudinal direction of the vasculature, a number of titled imaging slices 506 are obtained, as shown in FIG. 5B. As can be appreciated visually from FIG. 5B, fewer tilted imaging slices 508 may be utilized to provide a similar coverage of the imaging region 500 as compared to the imaging slices 506. In this example 7 tilted imaging slices 508 are shown.

In some aspects, imaging slices may be tilted by approximately 45 degrees with respect to an axial direction of the subject or an orientation of vasculature. For instance, imaging slices may be oriented away from a cranio-caudal direction. This would result in the number of slices required to scan an imaging region being reduced by a factor of √2 compared with the standard axial slice imaging. The scan time is reduced because fewer slices are required. The scan time reduction can be proportion to the reduced number of slices. However, it may be appreciated that the imaging slices may be tilted by any angle. Although an optimal balance between image quality and scan time reduction may be achieved using a tilt angle of 45 degrees, when imaging vasculature oriented substantially in the cranio-caudal direction, smaller or larger tilt angles may also achieve reduction in scan time compared to traditional axial imaging, albeit potentially to a lesser extent.

In tilting imaging slices, however, the central axis of the slices may no longer remain aligned with the longitudinal axis of the imaged blood vessels, particularly for the outer slices in an image set. The result is that the outer imaging slices in an image set may no longer fully encompass blood vessels of interest, as illustrated in the example of FIG. 5B. Hence, in accordance with aspects of the present disclosure, the field-of-view ("FOV") of one or more tilted imaging slices may also be shifted by one or more predetermined values.

Specifically referring to FIG. 5D, in addition to having a titling angle, a, the FOV of a first imaging slice 512 is shifted by a shift value, A, that brings it into a longitudinal alignment with a second imaging slice 514. In FIG. 5D, d is the gap between the center of the imaging slices. It is then readily apparent that loss of vascular coverage resulting from the tilted imaging slices 508 shown in FIG. 5B, may be overcome by also implementing shifted imaging slices 510 (shown in FIG. 5C), whose central axes would then remain aligned with the blood vessels being imaged.

The FOV shift, and other features, of one or more imaging slices forming an image set may be configured in dependence of the particulars of the imaged structures, such as an orientation of the subject's vasculature. For instance, in FIG. 5C, the FOV shift is zero for the center imaging slice and increases monotonically towards the outer slices of the image set. However, it may be appreciated that any combination of shifted and non-shifted imaging slices may be utilized to achieve maximal vascular coverage. For instance, a group of one or more tilted imaging slices may be shifted using one FOV shift value, while another group of one or more tilted imaging slices may be shifted using another FOV shift value, and so forth.

Figure 6:
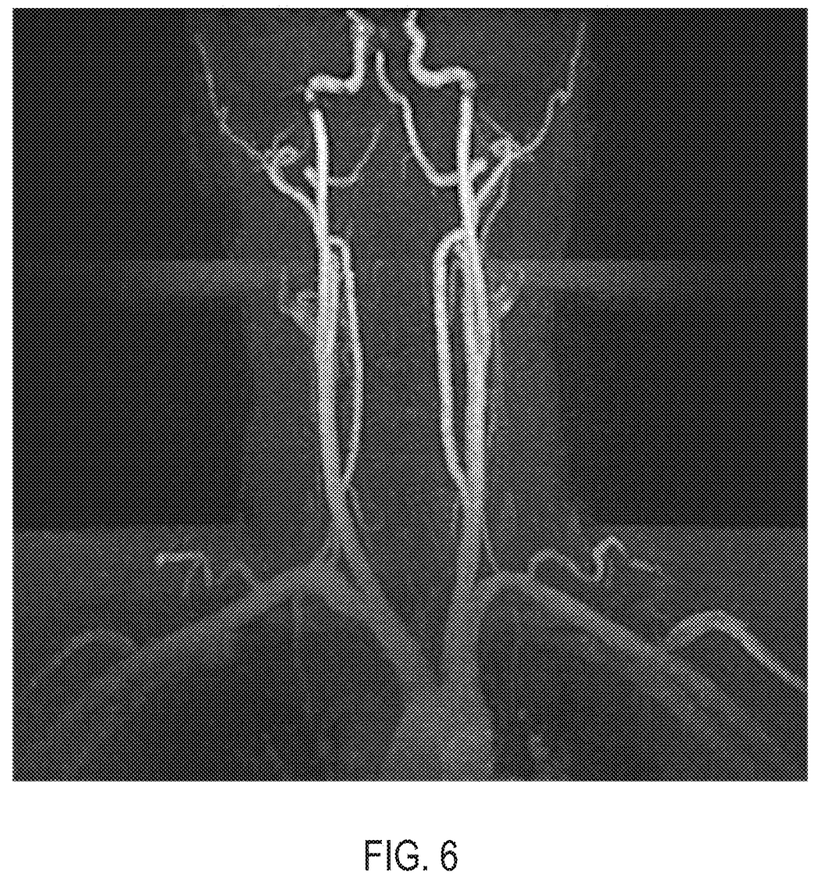
FIG. 6 is an example image of neck arteries obtained in accordance with the present disclosure.

By way of example, FIG. 6 shows an example image of a subject obtained using a maximum intensity projection from images acquired at four imaging stations. A total of 40 imaging slices tilted 45 degrees with respect to the axial plane of the subject was obtained for each station. Compared to a standard axial scan, the titled scan reduced the scanning time by 41%, representing a significant time savings.

Figure 1:
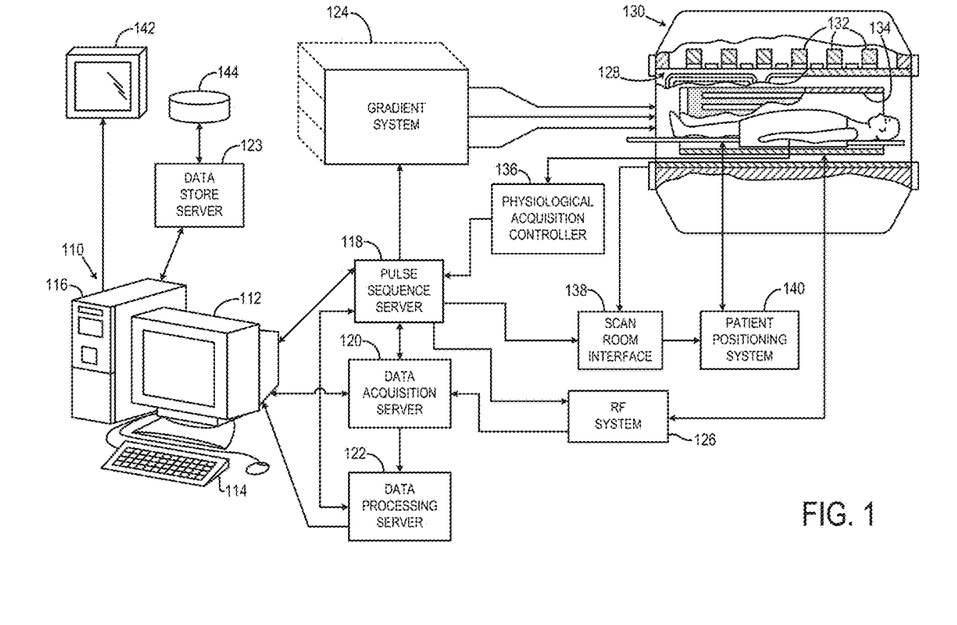
FIG. 1 is a block diagram of an example MRI system for use in accordance with aspects of the present disclosure.

Referring particularly to FIG. 1, an example MRI system, for use in accordance with aspects of the present disclosure, is shown. The MRI system includes a workstation 110 having a display 112 and a keyboard 114. The workstation 110 includes a processor 116 that is a commercially available programmable machine running a commercially available operating system. The workstation 110 provides the operator interface that enables scan prescriptions to be entered into the MRI system. The workstation 110 is coupled to four servers: a pulse sequence server 118; a data acquisition server 120; a data processing server 122, and a data store server 123. The workstation 110 and each server 118, 120, 122 and 123 are connected to communicate with each other.

The pulse sequence server 118 functions in response to instructions downloaded from the workstation 110 to operate a gradient system 124 and a radio frequency ("RF") system 126. Gradient waveforms necessary to perform the prescribed scan are produced and applied to the gradient system 124 that excites gradient coils in an assembly 128 to produce the magnetic field gradients $G_x$, $G_y$, and $G_z$ used for position encoding MR signals. The gradient coil assembly 128 forms part of a magnet assembly 130 that includes a polarizing magnet 132 and a whole-body RF coil 134.

RF excitation waveforms are applied to the RF coil 134 by the RF system 126 to perform the prescribed magnetic resonance pulse sequence. Responsive MR signals detected by the RF coil 134 or a separate local coil (not shown in FIG. 1) are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays (not shown in FIG. 1).

The RF system 126 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi = \tan^{-1}\left(\frac{Q}{I}\right).$$

The pulse sequence server 118 also optionally receives patient data from a physiological acquisition controller 136. The controller 136 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heartbeat.

The pulse sequence server 118 also connects to a scan room interface circuit 138 that receives signals from various sensors associated with the condition of the patient and the magnet system. It is also through the scan room interface circuit 138 that a patient positioning system 140 receives commands to move the patient to desired positions during the scan.

The digitized MR signal samples produced by the RF system 126 are received by the data acquisition server 120. The data acquisition server 120 operates in response to instructions downloaded from the workstation 110 to receive the real-time MR data and provide buffer storage such that no data is lost by data overrun. In some scans the data acquisition server 120 does little more than pass the acquired MR data to the data processor server 122. However, in scans that require information derived from acquired MR data to control the further performance of the scan, the data acquisition server 120 is programmed to produce such information and convey it to the pulse sequence server 118. For example, during prescans MR data is acquired and used to calibrate the pulse sequence performed by the pulse sequence server 118. Also, navigator signals may be acquired during a scan and used to adjust RF or gradient system operating parameters or to control the view order in which k-space is sampled. Although not necessary for non-contrast magnetic resonance angiography, in accordance with aspects of the present disclosure, the data acquisition server 120 may be employed to process MR signals to detect the arrival of contrast agent. In all these examples the data acquisition server 120 acquires MR data and processes it in real-time to produce information that is used to control the scan.

The data processing server 122 receives MR data from the data acquisition server 120 and processes it in accordance with instructions downloaded from the workstation 110. Such processing may include, for example: Fourier transformation of raw k-space MR data to produce two or three-dimensional images; the application of filters to a reconstructed image; the performance of a back projection image reconstruction of acquired MR data; the calculation of functional MR images; the calculation of motion or flow images, etc.

Images reconstructed by the data processing server 122 are conveyed back to the workstation 110 where they are stored. Real-time images are stored in a data base memory cache (not shown) from which they may be output to operator display 112 or a display 142 that is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

In some aspects, as will be described, a method for non-contrast enhanced MRA that is substantially insensitive to variations in arterial flow velocity or heart rate and that further substantially suppresses unwanted venous signals in prescribed imaging slices may be advantageous. As such, a method for accurately depicting normal and diseased arteries despite a wide range of flow velocities may be utilized, which synchronizes a quiescent interval to the period of rapid, systolic arterial blood flow so as to maximize flow-related enhancement into the imaging slice. Additionally, the method may also synchronize data acquisition to occur during diastole when arterial blood is stationary or flowing relatively slowly into a prescribed imaging slice. If venous blood flow is flowing in a cranial direction and arterial blood flow in a caudal direction, as is the case for the peripheral arteries, this venous suppression can be further augmented by the application of saturation pulses prior to the QI. The saturation pulses are applied not only in the imaging slice, but also in a slab contiguous with and caudal to the imaging slice. Likewise, when venous blood is flowing in a caudal direction and arterial blood in the cranial direction, as is the case in the internal jugular vein and common carotid artery, respectively, the slab may be selected to be contiguous with and cranial to the imaging slice. In this manner, saturated venous spins and unsaturated arterial spins can flow into the imaging slice over the duration of the QI.

In some aspects, data may be acquired in a single shot, reducing motion artifacts and allowing a series of 2D imaging slices to be obtained within a single breath-hold. As will be appreciated one of ordinary skill in the art, imaging methods described below are readily amenable to implementing tilted and/or shifted imaging slices, affording appreciable scanning time savings, in accordance with aspects of the present disclosure.

Figure 2:
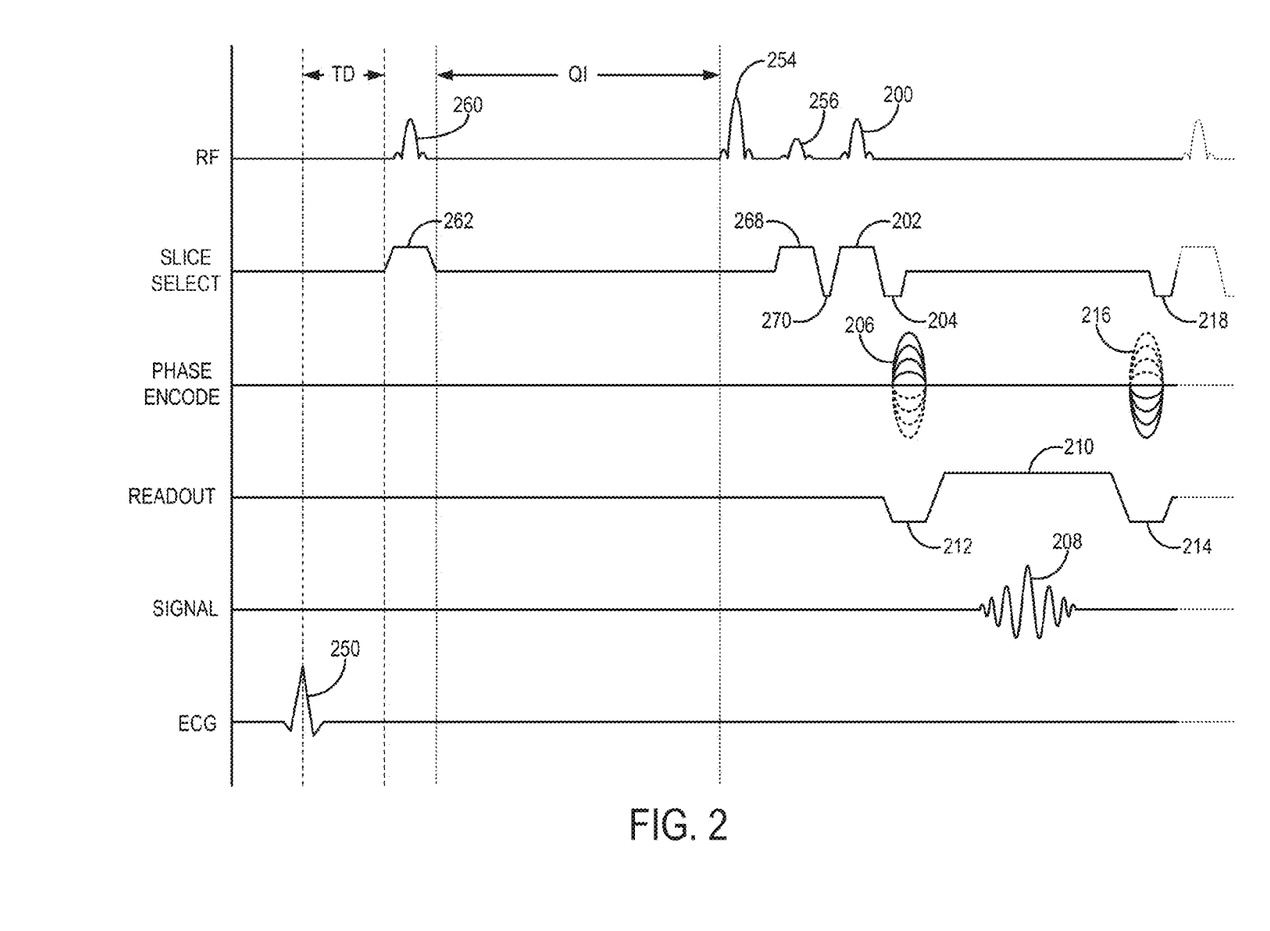
FIG. 2 is a pictorial representation of a pulse sequence performed by the MRI system of FIG. 1 in accordance with the present disclosure.

Referring now particularly to FIG. 2, a pulse sequence in accordance with the present disclosure is provided. The pulse sequence is cardiac gated, such that the acquisition of k-space data is timed with respect to the flow of arterial blood. Specifically, the pulse sequence is timed to be played out with respect to the peak of the R-wave 250 in a concurrently acquired echocardiogram ("ECG"). It should be appreciated by those skilled in the art, however, that other methods for cardiac synchronization of the following pulse than relying on an ECG signal are possible. For example, cardiac synchronization can be achieved using self-gating techniques that rely on measurement of flow signal or phase. Turning now to the pulse sequence, a slice-selective RF saturation pulse 260 is first played out in the presence of a slice-selective gradient 262 The application of this slice-selective RF saturation pulse 260 has the effect of suppressing the signals from background tissues as well as those venous spins that are present in the prescribed slice. The flip angle for this slice-selective RF saturation pulse 260 is typically about 90 degrees; however, larger or smaller flip angles may be desirable in some circumstances. The slice-selective RF saturation pulse 260 is timed to occur at a preset time delay ("TD") after the occurrence of the R-wave 250. For example, TD is set to 100 ms.

The duration of time that is allowed to pass after the application of the slice-selective RF saturation pulse 260 is herein referred to as the "quiescent interval" ("QI"). This duration of time is specifically tailored to coincide with the rapid inflow of arterial blood into a prescribed imaging slice, and so that the zero line of k-space is acquired during the slow, diastolic inflow of arterial blood into the imaging slice. More particularly, a central portion of k-space is sampled during the slow, diastolic inflow of arterial blood into the imaging slice before the peripheral regions of k-space are sampled. The result of this is a substantial suppression of flow-based image artifacts. Put another way, this provides a method that is substantially insensitive to flow velocities in the prescribed image slice. Moreover, the QI allows for a maximal inflow of unsaturated arterial spins into the imaging slice, such that an improved discrimination of arterial spins is provided in the resultant images. This is even so when the patient's vasculature is significantly impacted by vascular diseases such as peripheral vascular disease ("PVD"). Exemplary values of QI in this configuration of the pulse sequence are on the order of 260 ms.

After the QI has passed, the pulse sequence proceeds with data acquisition, which is accomplished, for example, with a single shot balanced steady-state free procession ("SSFP") gradient echo pulse sequence. First, a spectrally selective fat saturation RF pulse 254 may be applied to further suppress unwanted MR signals originating from fat tissue. This is subsequently followed by a slice-selective $\alpha/2$ magnetization RF pulse 256 that is played out in the presence of a slice-selective gradient 268, where $\alpha$ is a user selected flip angle. The slice-selective gradient includes a rephasing lobe 270 that acts to mitigate unwanted phase accruals that occur during the application of the slice-selective gradient 268. This portion of the pulse sequence includes a slice-selective RF excitation pulse 200 that is played out in the presence of a slice-selective gradient pulse 202 to produce transverse magnetization in a prescribed slice. The slice-selective gradient includes a rephasing lobe 204 that acts to mitigate unwanted phase accruals that occur during the application of the slice-selective gradient 202. After excitation of the spins in the slice, a phase encoding gradient pulse 206 is applied to position encode the MR signal 208 along one direction in the slice. A readout gradient pulse 210 is also applied after a dephasing gradient lobe 212 to position encode the MR signal 206 along a second, orthogonal direction in the slice. Like the slice-selective gradient 202, the readout gradient 210 also includes a rephasing lobe 214 that acts to mitigate unwanted phase accruals.

To maintain the steady state condition, the integrals along the three gradients each sum to zero during the repetition time ("TR") period. To accomplish this, a rewinder gradient lobe 216 that is equal in amplitude, but opposite in polarity of the phase encoding gradient 206, is played out along the phase encoding gradient axis. Likewise, a dephasing lobe 218 is added to the slice select gradient axis, such that the dephasing lobe 218 precedes the repetition of the slice-selective gradient 202 in the next TR period. As is well known in the art, the reading out of MR signals following the single shot of the RF excitation pulse 200 is repeated and the amplitude of the phase encoding gradient 206 and its equal, but opposite rewinder 216 are stepped through a set of values to sample 2D k-space in a prescribed manner. It should be appreciated by those skilled in the art that any number of data acquisition schemes can be employed to acquire k-space data instead of balanced SSFP. For example, spoiled gradient echo, spiral acquisition, or echo planar imaging ("EPI") pulse sequences can alternatively be utilized.

Figure 3:
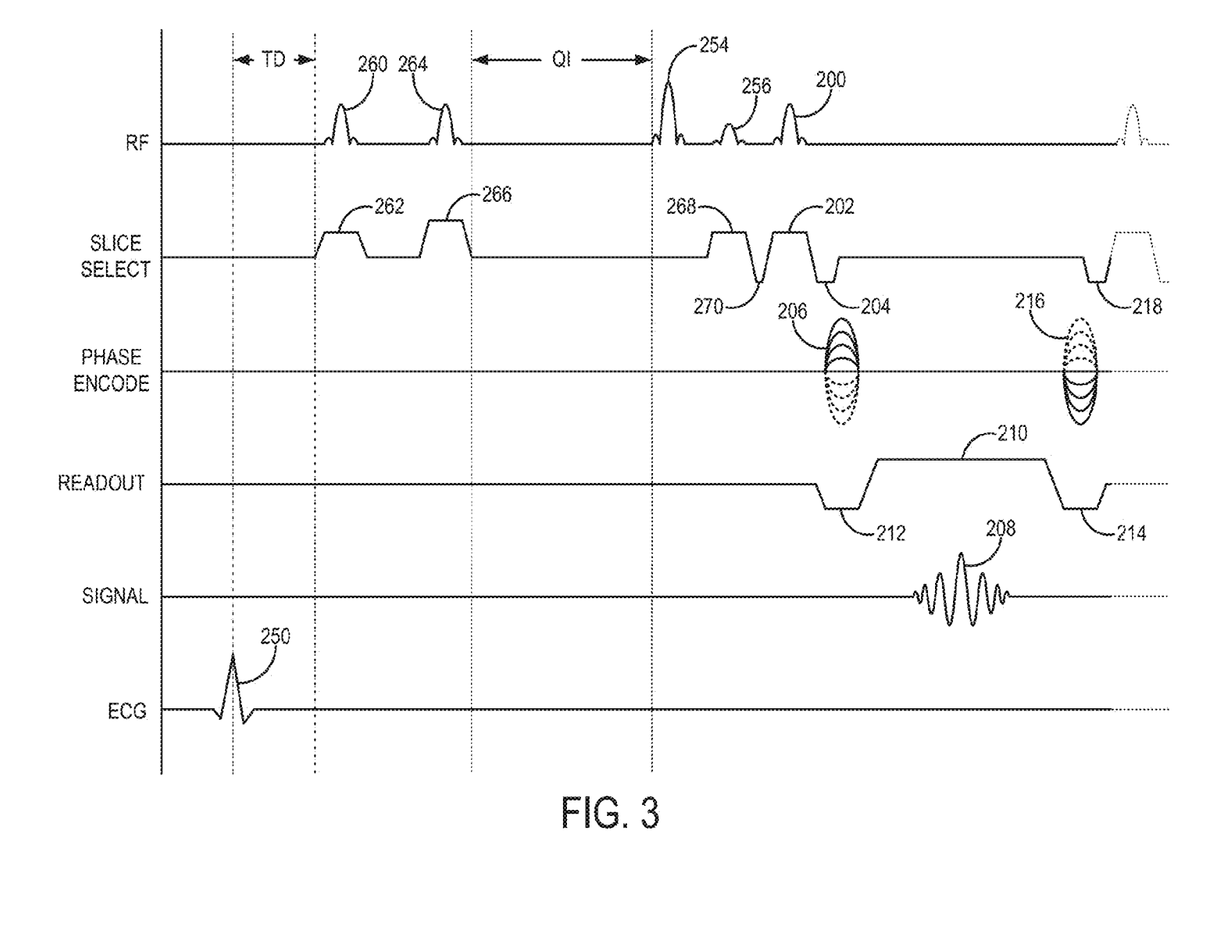
FIG. 3 is a pictorial representation of a pulse sequence performed by the MRI system of FIG. 1 in accordance with the present disclosure.

Referring now particularly to FIG. 3, another pulse sequence employed in accordance with the present disclosure is provided. This pulse sequence is also cardiac gated, such that the acquisition of k-space data is timed with respect to the flow of arterial blood. Specifically, the pulse sequence is timed to be played out with respect to the peak of the R-wave 250 in a concurrently acquired echocardiogram ("ECG"). However, the data acquisition portion of the pulse sequence is preceded by the application of two RF saturation pulses. By employing RF saturation pulses instead of inversion recovery pulses, the longitudinal magnetization is always reset to zero prior to the beginning of the QI. This is not necessarily the case when employing inversion recovery-based methods, as residual longitudinal magnetization resulting from inadequate inversion may confound the subsequently detected MR signals. Moreover, by always resetting the longitudinal magnetization of the slice to zero, the use of a slice-selective RF saturation pulse ensures that the tissue signal remains substantially uniform across different slices despite variations in the R-R interval due to cardiac arrhythmias. This is not the case with inversion-recovery based methods.

First, a slice-selective RF saturation pulse 260 is played out in the presence of a slice-selective gradient 262. The application of this slice-selective RF saturation pulse 260 has the effect of suppressing the signals from background tissues as well as those venous spins that are present in the prescribed slice. The slice-selective RF saturation pulse 260 is timed to occur at a preset time delay ("TD") after the occurrence of the R-wave 250. For example, TD is set to 100 ms.

To suppress signals from venous spins that will flow into the prescribed slice, a second, slab-selective RF saturation pulse 264 is played out in the presence of a slab-selective gradient 266. The slab-selective RF saturation pulse 264 has the effect of suppressing venous signals in a slab that is contiguous with the prescribed imaging slice. Specifically, when imaging the peripheral arteries, the prescribed slab is chosen to be caudal to, and contiguous with, the prescribed imaging slice such that saturated venous blood flows into the imaging slice in the caudal-cranial direction while unsaturated arterial spins flow into the imaging slice in the cranial-caudal direction. Similarly, when imaging, for example, the carotid artery, the prescribed slab is chosen to be cranial to, and contiguous with, the prescribed imaging slice such that saturated venous blood flows into the imaging slice in the cranial-caudal direction while unsaturated arterial spins flow into the imaging slice in the caudal-cranial direction. Exemplary RF excitation slab thicknesses are on the order of 150 mm; however, it will be appreciated by those skilled in the art that other thicknesses can be selected depending on the intended application and subject at hand. It will also be appreciated that in some circumstances it may be desirable to shift the RF excitation slab so that it is not contiguous with the imaging slice.

In this alternate configuration of the pulse sequence, the QI is defined as the duration of time occurring after the application of the slab-selective RF saturation pulse 264 and before the fat saturation pulse 254. Like the previously described QI, however, this duration of time is specifically tailored so that the zero line of k-space is acquired during the slow, diastolic inflow of arterial blood into the prescribed imaging slice. As described above, the result of allowing the QI to pass before data acquisition is a substantial suppression of flow-based image artifacts. Put another way, this provides a method that is substantially insensitive to flow velocities in the prescribed image slice. Exemplary values of QI in this configuration of the pulse sequence are on the order of 250 ms. The proceeding data acquisition is played out similar to the above-described pulse sequence, which is so described with respect to FIG. 2.

Unlike previous methods that rely on multi-shot acquisitions, the repetition time of the pulse sequences employed in accordance with the present disclosure may be significantly shorter than, say, the 30 ms typically required of such multi-shot sequences. In this manner, the overall scan time is less than the several seconds required of previous methods. This allows the method of the present disclosure to acquire the desired image data without becoming significantly sensitive to subject motion. Additionally, the shortened data acquisition period provided by the present disclosure allows image data to be acquired during only a portion of arterial flow, such that variations in flow velocity during the cardiac cycle do not confound the acquired MR signals.

Figure 4A:
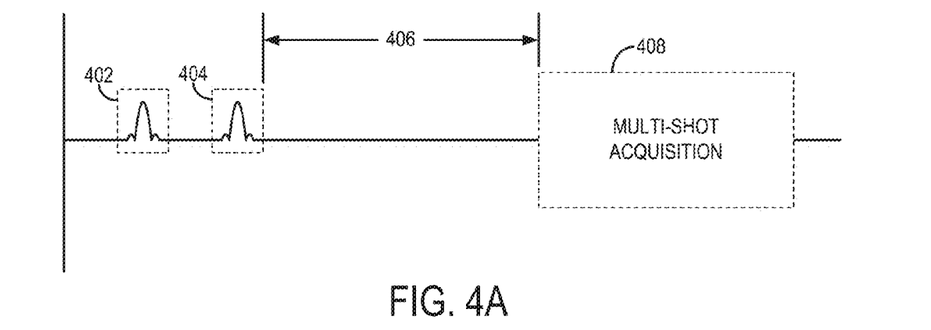
FIG. 4A is an example of a pulse sequence that can be performed by the MRI system of FIG. 1 in accordance with the present disclosure.
Figure 4B:
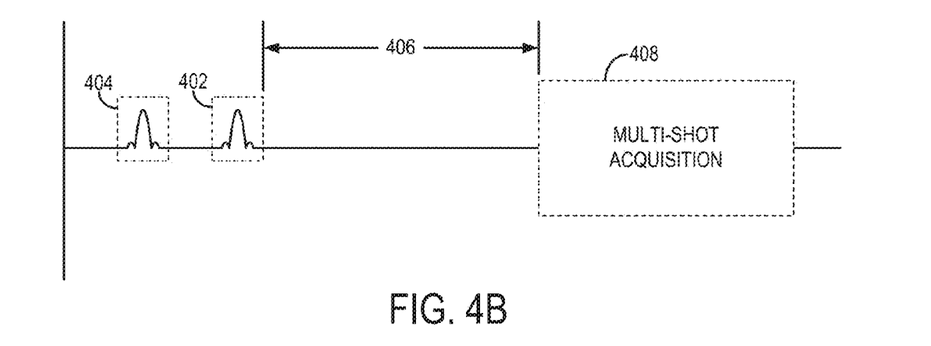
FIG. 4B is another example of a pulse sequence that can be performed by the MRI system of FIG. 1 in accordance with the present disclosure.

In some embodiments, a multi-shot acquisition can be implemented, however, to achieve an echo train length that is sufficiently short so as to substantially suppress blood flow-related artifacts. Examples of pulse sequences that implement a multi-shot acquisition are illustrated in FIGS. 4A and 4B. This pulse sequence includes the application of one or more RF saturation pulses 402 to the imaging slice, and the application of one or more RF saturation pulses 404 to a region outside of the imaging slice. In doing so, magnetic resonance signals in the imaging slice are at least partially suppressed, as are magnetic resonance signals in the region outside of the imaging slice. A period of time 406 is then allowed to pass, during which no RF pulses are applied. The period of time 406 is sufficiently long to allow saturated, undesired vascular spins from the region outside the imaging slice to flow into the imaging slice, and to allow unsaturated, desired vascular spins from outside the imaging slice to flow into the imaging slice. As shown in FIG. 4A, the in-slice RF saturation pulses 402 can be applied before the out-of-slice RF saturation pulses 404, or as illustrated in FIG. 4B, the order in which these RF saturation pulses 402, 404 are applied can be switched.

Data is then acquired from the imaging slice using a multi-shot acquisition 408. For instance, an excitation RF pulse is applied to the imaging slice and k-space data is acquired by sampling k-space using a multi-shot acquisition scheme. Examples of multi-shot acquisitions that can be used include, but are not limited to, steady-state free precession ("SSFP") sequences, including balanced SSFP ("bSSFP") sequences. The multi-shot acquisition 408 has an echo train length ("ETL") that is sufficiently short so as to substantially suppress blood flow-related artifacts. Advantageously, using such a multi-shot acquisition results in being able to acquire k-space data without cardiac gating. The k-space data is acquired by sampling k-space along one or more k-space trajectories. These k-space trajectories can be, for example, radial, spiral, or Cartesian trajectories.

The pulse sequence can be repeated to acquire k-space data from multiple different slice locations. These multiple images can be processed to produce an angiographic image, as is known in the art. Additionally, the pulse sequence can be repeated to acquire k-space data from a plurality of different segments of k-space in each repetition. Images can then be reconstructed using only a subset of these different segments.

Motion-related artifacts, such as blood flow-related artifacts, can be identified or otherwise detected in the k-space data and then corrected for before reconstructing images. As one example, when k-space data is acquired as a plurality of different segments, as described above, these data segments can be analyzed to detect whether motion-related artifacts are present in the acquired data. Similarly, navigator data can be separately acquired and used to detect whether motion-related artifacts are present in the k-space data. When such artifacts are present, the k-space data can be corrected using motion correction techniques known in the art.

The present invention has been described in terms of one or more preferred embodiments, and it should be appreciated that many equivalents, alternatives, variations, and modifications, aside from those expressly stated, are possible and within the scope of the invention. For example, it should be appreciated by those skilled in the art that a plurality of different saturation pulses may be employed prior to the beginning of the QI, with an appropriate change in QI. For example, as more saturation pulses are added, QI may decrease down to about 100 ms. Additionally, the specific order of the RF saturation pulses can be altered, such that a slab-selective saturation pulse is applied prior to a slice-selective saturation pulse, without significantly changing the resultant image contrast.

What is claimed is:

1. A method for performing a non-contrast-enhanced magnetic resonance angiography ("MRA") for a subject, the method comprising:
   a) directing a magnetic resonance imaging ("MRI") system to perform a pulse sequence to acquire k-space data from imaging slices that are oriented away from an axial direction of the subject, the pulse sequence comprising:
      i) applying at least one radio frequency ("RF") saturation pulse to a selected region in the subject at least partially suppressing magnetic resonance signals therein;
      ii) applying at least one RF saturation pulse to an imaging slice outside the selected region at least partially suppressing magnetic resonance signals therein;
      iii) waiting a period of time sufficiently long to allow saturated vascular spins from the selected region to flow into the imaging slice and to allow unsaturated vascular spins from outside the selected region to flow into the imaging slice;
      iv) acquiring k-space data from the imaging slice following the period of time;
   b) repeating steps a)i) through a)iv) for a plurality of imaging slices, wherein a field-of-view ("FOV") of at least one of the plurality of imaging slices is shifted by a predetermined value; and
   c) reconstructing, using the acquired k-space data, one or more angiographic images indicative of the subject's vasculature.

2. The method as recited in claim 1 in which step a)iv) includes acquiring k-space data from one segment of k-space, and step a) is repeated a plurality of times to acquire k-space data from different segments of k-space.

3. The method as recited in claim 2 in which step c) includes reconstructing from the acquired k-space data, a plurality of images that depict the unsaturated vascular spins in the subject's vasculature, each of the plurality of images corresponding to a different slice location.

4. The method as recited in claim 3 further comprising producing the one or more angiographic images from the plurality of images.

5. The method as recited in claim 2 in which step c) includes reconstructing the image from k-space data corresponding to only a subset of the different segments of k-space.

6. The method as recited in claim 2 further comprising detecting whether motion-related artifacts are present in the acquired k-space data by analyzing the k-space data associated with the different segments of k-space.

7. The method as recited in claim 6 further comprising correcting the acquired k-space data when motion-related artifacts are present in the acquired k-space data.

8. The method as recited in claim 6 in which the motion-related artifacts are flow-related artifacts.

9. The method as recited in claim 1 further comprising acquiring navigator data and detecting whether motion-related artifacts are present in the acquired k-space data by analyzing the navigator data.

10. The method as recited in claim 9 further comprising correcting the acquired k-space data when motion-related artifacts are present in the acquired k-space data.

11. The method as recited in claim 1 in which step a)iv) includes acquiring k-space data by sampling k-space along at least one k-space trajectory.

12. The method as recited in claim 11 in which the at least one k-space trajectory is at least one of a radial trajectory, a spiral trajectory, and a Cartesian trajectory.

13. The method as recited in claim 1 in which step a)i) is performed before step a)ii), and in which the period of time in step a)iii) occurs after step a)ii) is performed.

14. The method as recited in claim 1 in which step a)ii) is performed before step a)i), and in which the period of time in step a)iii) occurs after step a)i) is performed.

15. The method as recited in claim 1 in which step a)iv) includes acquiring k-space data by sampling k-space using a single-shot acquisition or a multi-shot acquisition.

16. The method as recited in claim 15, wherein the multi-shot acquisition is a balanced SSFP ("bSSFP") acquisition or a spoiled gradient-echo acquisition.

17. The method as recited in claim 1 in which the period of time in step a)iii) is between 100 and 1000 milliseconds.

18. The method as recited in claim 1 in which the period of time in step a)iii) is selected such that step a)iv) occurs during slow diastolic inflow of unsaturated vascular spins associated with arterial blood into the prescribed imaging slice.

19. The method as recited in claim 1 in which the imaging slices are oriented away from the axial direction of the subject by a tilt angle up to 45 degrees.

20. The method as recited in claim 1 further comprising determining the predetermined value based at least on an orientation of the subject's vasculature.

* * * * *